United States Patent [19]

Ueda et al.

[11] Patent Number: 5,356,790
[45] Date of Patent: Oct. 18, 1994

[54] HIGHLY SENSITIVE ASSAY METHOD FOR MYO-INOSITOL, COMPOSITION FOR PRACTICING SAME, NOVEL MYO-INOSITOL DEHYDROGENASE, AND PROCESS FOR PRODUCING SAME

[75] Inventors: Shigeru Ueda; Mamoru Takahashi; Hideo Misaki; Shigeyuki Imamura; Kazuo Matsuura, all of Shizuoka, Japan

[73] Assignee: Asahi Kasei Kogyo Kabushiki Kaisha, Osaka, Japan

[21] Appl. No.: 106,693

[22] Filed: Aug. 16, 1993

Related U.S. Application Data

[63] Continuation of Ser. No. 761,465, Sep. 18, 1991, abandoned.

[30] Foreign Application Priority Data

Sep. 18, 1990 [JP] Japan .................................. 2-249775
Sep. 18, 1990 [JP] Japan .................................. 2-249776

[51] Int. Cl.$^5$ .......................... C12Q 1/26; C12Q 1/32; C12N 11/00; C07H 1/00
[52] U.S. Cl. ........................................ 435/26; 435/25; 435/16; 435/10; 435/174; 435/175; 435/178; 436/817; 536/4.1; 536/1.11; 536/26.24; 568/347
[58] Field of Search ................... 435/26, 25, 16, 10, 435/174, 175, 178; 536/1.1, 4.1; 568/347; 436/817

[56] References Cited

U.S. PATENT DOCUMENTS

| | | | |
|---|---|---|---|
| 4,120,755 | 10/1978 | Pierre et al. | 435/14 |
| 4,791,057 | 12/1988 | Misaki et al. | 435/25 |
| 4,898,986 | 2/1990 | Horii et al. | 568/376 |
| 5,004,838 | 4/1991 | Horii et al. | 568/347 |
| 5,032,506 | 7/1991 | Palmer et al. | 435/25 |
| 5,036,000 | 7/1991 | Palmer et al. | 435/10 |
| 5,091,596 | 2/1992 | Kennington et al. | 568/833 |
| 5,206,146 | 4/1993 | Misaki et al. | 435/16 |

OTHER PUBLICATIONS

"Purification and Properties of Bacillus subtilis Inositol Dehydrogenase", *Journal of Biological Chemistry*, vol. 254, No. 16, 1979, By R. Ramaley et al., pp. 7684–7690.
"A Sensitive Bioluminescene Assay for myo-Inositol",
(List continued on next page.)

*Primary Examiner*—Michael G. Wityshyn
*Assistant Examiner*—Louise N. Leary
*Attorney, Agent, or Firm*—Young & Thompson

[57] ABSTRACT

Myo-inositol in a specimen is assayed by reacting a specimen containing myo-inositol with:
a) myo-inositol dehydrogenase using a thio-NADP group or thio-NAD group and an NADP group or NAD group as coenzymes, and which catalyzes a reversible reaction forming myo-inosose from myo-inositol,
b) $A_1$ and
c) $B_1$
to effect a cycling reaction

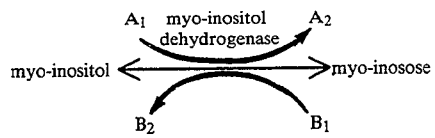

wherein $A_1$ is a thio-NADP group, thio-NAD group, NADP group or NAD group, $A_2$ is a reduced form of $A_1$, when $A_1$ is a thio-NADP group or thio-NAD group, $B_1$ is a reduced NADP group or reduced NAD group and when $A_1$ is an NADP group or NAD group, $B_1$ is a reduced thio-NADP group or reduced thio-NAD group, and wherein $B_2$ is an oxidized form of $B_1$. The change in the amount of $A_2$ generated or $B_1$ consumed by the cycling reaction is measured to perform the assay. A composition for performing the assay comprises the above myo-inositol dehydrogenase, as well as the above components $A_1$ and $B_1$. The myo-inositol dehydrogenase can be produced by culturing a suitable microorganism belonging to genus Bacillus, particularly Bacillus sp. No. 3 FERM BP-3013.

5 Claims, 8 Drawing Sheets

OTHER PUBLICATIONS

*Analytical Biochemistry,* vol. 158, No. 1, Oct. 1986, pp. 59–63.

"Determination of Myo–Inositol In A Flow–Injection System with Co–Immobilized Enzyme Reactors and Amperometric Detection", Analytica Chimica Acta, vol. 206, 1988, By B. Olsson et al., pp. 49–55.

"An Enzymatic Fluorimetric Assay for Myo–Inositol", Analytical *Biochemistry,* vol. 141, 1984, By L. Mac-Gregor et al., pp. 382–389.

"Clinical Chem.", vol. 24, No. 11, 1988, pp. 1448–1455. "Inositol Dehydrogenase from Aerobacter Aerogenes", *Methods in Enzynology,* vol. 36, By J. Larner, pp. 326–329 (1962).

"Inositol Dehydrogenase From the Yeast Cryptococcus Melibiosum" *Biochimica et Biophysca Acta,* No. 293, 1973, By M. Vidal–Leiria et al., pp. 294–303.

"The Identification of MYO–Inositol; NAD(P)+Oxidoreductase in Mammalian Brian", *Biochemical and Biophysical Research Communications* vol. 68, No. 4, 1976, By P. Hipps et al., pp. 1132–1139.

"Fluorometric Determination of Myo–Inositol in Blood Using High Performance Liquid Chromatography", *Proceeding of Japan Clinical Chemistry Annual Meeting,* No. 28, 1988, By Y. Inamoto et al., p. 116.

"The Pathway of myo–Inositol Degradation in Aerobacter aerogenes" *The Journal of Biological Chemistry,* vol. 241, No. 4, Feb. 1966, By T. Berman et al., pp. 800–807.

Leiria et al., "Inositol Dehydrogenase from the Yeast Cryptococcus Melibiosum"; Biochimica et Biophysica Acta, 293 (1973) pp. 295–303.

Berman et al.; "The Pathway of myo–Inositol Degradation in Aerobacter Aerogenes"; Journal of Biological Chemistry; vol. 241; No. 4; 800–806 (1966).

Hipps et al.; "The Identification of Myo–Inositol": NAD(P)+ Oxidoreductase in Mammalian Brian; Biochemical & Biophysical Research Communications; vol. 68, No. 4 (1976); pp. 1133–1138.

Merck Index; 10th Edition, pp. 722–723; 1983.

Larner, J.; "Inositol Dehydrogenase from Aerobacter aerogenes Inositol $+DPN^+ \rightleftharpoons$ Inosset $DPNH+H^+$"; Enzymes of Carbohydrate Metabolism; pp. 326–329 (1962).

HIGHLY SENSITIVE ASSAY METHOD FOR MYO-INOSITOL, COMPOSITION FOR PRACTICING SAME, NOVEL MYO-INOSITOL DEHYDROGENASE, AND PROCESS FOR PRODUCING SAME

This application is a continuation of application Ser. No. 07/761,465, filed Sep. 18, 1991, now abandoned.

FIELD OF THE INVENTION

This invention relates to a highly sensitive assay method for myo-inositol, especially myo-inositol contained in a specimen, and to a composition for assaying myo-inositol, and to a novel myo-inositol dehydrogenase and to a process for its production.

BACKGROUND OF THE INVENTION

Myo-inositol is one of nine isomers of inositol and is a stable cyclic alcohol. In humans, myo-inositol is supplied exogenously approximately one gram per day from food and endogenously approximately two grams per day by renal biosynthesis.

The blood level of myo-inositol is kept constant by a balance of intake into the cells and renal excretion, reabsorption and oxidation.

The plasma level of myo-inositol is increased upon the occurrence of renal functional disorder (Clinical Chem., 24(11); 1448-1455 (1988)). Hence, renal function can be monitored by measuring the level of myo-inositol in the blood. and the amount of change in any of the coenzymes is measured as a difference in maximum absorption of both of reduced coenzymes. In this way, the amount of myo-inositol in the specimen can be quite precisely measured.

More particularly, we have discovered a highly sensitive assay method for myo-inositol, which comprises reacting a specimen with a reagent containing (1) myo-inositol dehydrogenase using one of coenzymes of thionicotinamide adonine dinucleotide phosphate group (hereinafter designated thio-NADP group) or thionicotinamide adenine dinucleotide group (hereinafter designated thio-NAD group) and one of nicotinamide adonine dinucleotide phosphate group (hereinafter designated NADP group) or nicotinamide adonine dinucleotide group (hereinafter designated NAD group) and which catalyzes a reversible reaction forming myo-inosose from a substrate of myo-inositol, (2) $A_1$ and (3) $B_1$ to effect a cycling reaction

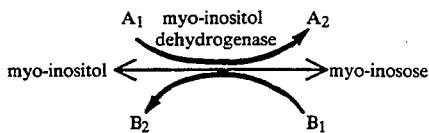

wherein $A_1$ is thio-NADP group, thio-NAD group, NADP group or NAD group, $A_2$ is a reduced form of $A_1$, when $A_1$ is thio-NADP group or thio-NAD group, $B_1$ is reduced NADP group or reduced NAD group and when $A_1$ is NADP group or NAD group, $B_1$ is reduced thio-NADP group or thio-NAD, and $B_2$ is an oxidized form of $B_1$. The change in the amount of $A_2$ or $B_1$, which results from the above reaction, is then measured.

The present invention also provides a composition for assaying myo-inositol consisting essentially of the above components (1)-(3).

The present invention further provides a novel enzyme myo-inositol dehydrogenase.

Finally, the present invention provides a process for the production of the novel enzyme myo-inositol dehydrogenase.

DETAILED DESCRIPTION OF THE INVENTION

Figure 1:
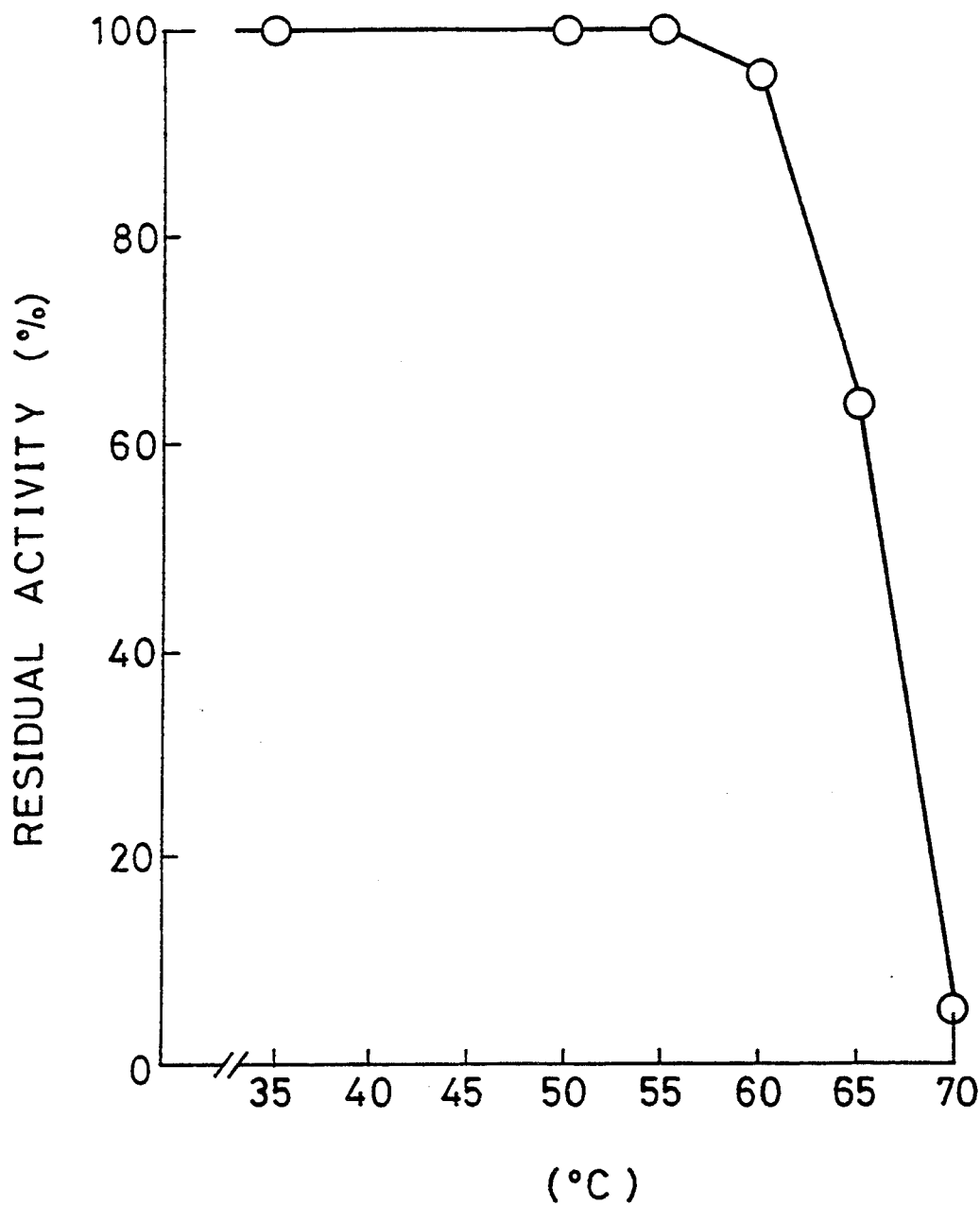
FIG. 1 is a curve of the heat stability of the novel myo-inositol dehydrogenase.

In the present invention, any type of myo-inositol dehydrogenase can be used that has the properties hereinabove. Examples of myo-inositol dehydrogenase suitable for use in the present invention are described in Enzyme Handbook (Asakura Publishing Co., Tokyo) and are myo-inositol dehydrogenase produced by the following microorganisms:

Aerobacter aerogenes (J. Biol. Chem., 241, 800-806 (1966)); Klebsiella pneumoniae, Serratia marcescens, Cryptococcus melibiosum (Biochim. Biophys. Acta., 293, 295-303 (1973)); and bovine brain (Biochem. Biophys. Res. Comm., 68, 1133-1138 (1976)); Bacillus sp. No. 3 (product of Toyo Jozo Co.)

Among these, Aerobacter aerogenes, Klebsiella pneumoniae and Serratia marcescens are known as etiologic microorganisms for pneumonia and opportunistic infections (Standard Microbiology, 2nd edn., pp. 209-212, Igaku Shoin Publishing Co., Tokyo, 1984) resistant to chemotherapeutics and antibiotics. Culturing these microorganisms on an industrial scale is substantially impossible. The Km value of myo-inositol dehydrogenase produced by yeast Cryptococcus melibiosum is approximately 11.0 mM for myo-inositol and approximately 0.07 mM for NAD, which are too high to permit a sufficient reaction rate (Enzyme Handbook, 1st edn., p. 6, Asakura Publishing Co., 1982).

We have made screening searches to find microorganisms which can produce myo-inositol dehydrogenase, with higher activity, with low Km value on substrate myo-inositol and NAD, which is stable and easily purified; and we have isolated a microorganism designated Bacillus sp. No. 3 from a soil sample in a hot spring area, Atagawa, Higashi-Izu-cho, Kamo-gun, Shizuoka-ken, Japan.

Myo-inositol dehydrogenase produced by Bacillus sp. No. 3 has Fan values for myo-inositol and NAD at pH 8.5 that are quite low, namely approximately 0.6 mM and 0.04 mM, respectively, with high reactivity. Moreover, the remaining activity after heating at 60° C. for 15 minutes in a buffer solution is above approximately 95%. This enzyme myo-inositol hydrogenase is a novel enzyme which can react with coenzyme NAD(P) groups and thio-NAD(P) groups.

This novel enzyme myo-inositol dehydrogenase can also be produced by myo-inositol dehydrogenase-producing microorganisms belonging to genus Bacillus, with isolation of the enzyme therefrom.

The present myo-inositol-producing microorganism belongs to genus Bacillus, and Bacillus sp. No. 3 which was isolated by the present inventors is the most preferable microorganism; however, this microorganism is to be understood as an example.

The taxonomical properties of this strain are as follows:

(A) Morphological properties

Round edges with straight or slightly curved bacillus. The size is 0.5–0.7×1.5–3.5 μm. Peritrical movement. Spore formations at an edge or subedge with sizes 0.8×1.0–2.0 μm of elliptical to oval spores are observed. Microbial cells are swollen with spores. No polymorphism.

(B) Growth on various media

Observations on various media, cultured for 1–2 days at 50–52° C., are as follows:

1. Nutrient agar plate medium: round and convex colonies. Smooth wet surface with round edges. Ocherous or plate ocherous. No formation of soluble pigment.
2. Nutrient agar slant medium: good growth with filiform. Ocherous to plate ocherous. No formation of soluble pigment.
3. Liquid medium (aqueous peptone): good growth with uniform turbidity.
4. Litmus milk medium: weakly acidic after 4–5 days. GC mole % in DNA: 41.9 mole % (HPLC method). Main isoprenoid quinone: MK - 7.

(C) Physiological properties

| | |
|---|---|
| Gram-strain | + |
| KOH reaction | − |
| Capsule formation | − |
| Acid fastness stain | − |
| OF-test (High Leifson) | NT |
| OF-test (nitrogen source: NH$_4$H$_2$PO$_4$) | F |
| Aerobic growth | + |
| Anaerobic growth | + |
| Growth temperature | |
| 70° C. | − |
| 60° C. | + |
| 37° C. | + |
| 30° C. | − |
| Halotolerant NaCl conc. (%) | |
| 0% | + |
| 3% | + |
| 5% | − |
| Growth pH | |
| pH 5.6 | − |
| pH 6.2 | + |
| pH 9.0 | + |
| Gelatin hydrolysis | − |
| Starch hydrolysis | (+) |
| Casein hydrolysis | − |
| Esculin hydrolysis | + |
| Cellulose hydrolysis | − |
| Tyrosine hydrolysis | − |
| Arginine hydrolysis | − |
| Catalase production | + |
| Oxidase production | + |
| Lecithinase production | − |
| Urease production (SSR) | − |
| Urease production (Chris) | − |
| Indol production | − |
| H$_2$S production (detection: lead acetate paper) | − |
| Acetoin production (K$_2$HPO$_4$) | − |
| Acetoin production (NaCl) | − |
| MR test | − |
| Nitrate reduction | |
| Gas detection | − |
| NO$_2$— | − |
| NO$_3$— | + |
| Utilization of Simmons medium | |
| Citrate | − |
| Malate | − |
| Maleate | − |
| Malonate | − |
| Propionate | − |
| Gluconate | − |
| Succinate | − |
| Utilization of Christenseen medium | |
| Citrate | + |
| Malate | − |
| Maleate | − |
| Malonate | − |
| Propionate | + |
| Gluconate | − |
| Succinate | − |
| Gas production from glucose | − |
| Acid formation from sugar | |
| Adonitol | − |
| L (+) arabinose | − |
| Cellobiose | + |
| Dulsitol | − |
| Meso-erythritol | − |
| Fructose | + |
| Fucose | + |
| Galactose | + |
| Glucose | + |
| Glycerin | + |
| Inositol | + |
| Inulin | + |
| Lactose | + |
| Maltose | + |
| Mannitol | + |
| Mannose | + |
| Melezitose | − |
| Melibiose | + |
| Raffinose | − |
| Rhamnose | + |
| D-ribose | + |
| Salicin | + |
| L-sorbose | − |
| Sorbitol | − |
| Starch | + |
| Saccharose | + |
| Xylose | − |
| Trehalose | + |

(+ = positive, (+) = weakly positive, − = negative, NT = not tested)

According to the above taxonomical properties, the microorganism displays the specific characteristics of Gram-positive Bacillus, namely, it is 0.5–0.7×1.5–3.5 μm in size, is peritrichal in movement, is spore forming with no polymorphism, promotes fermentative decomposition of glucose and acid formation, is catalase positive and oxidase positive, and is thermophilic and facultatively anaerobic.

Among Gram-positive bacilli with specific properties of spore formation and aerobic growth, the strain belongs to genus Bacillus.

According to *Bergey's Manual of Systematic Bacteriology*, Vol. 2, there are illustrated the following nine species of Bacillus with growth at high temperature (50° C.).

*Bacillus acidocaldarius, B. subtilis, B. badius, B. brevis, B. coagulans, B. licheniformis, B. pantothenticus, B. schegelli* and *B. stearothermophilus.*

Among these, microorganisms growing under anaerobic conditions are *B. coagulans* and *B. licheniformis.*

The taxonomic properties of Bacillus in comparison to those of the present strain, according to *Bergey's Manual* are illustrated by comparing *Bacillus coagulans* (hereinafter designated C) and *Bacillus licheniformis* (hereinafter designated L), as follows: (+ =positive, (+)=weakly positive, — =negative, d=not identified as + or —, ND=no data)

| | C | L | The Present Strain |
|---|---|---|---|
| Oxidase production | — | d | + |
| Swelling with spores | d | — | + |
| Anaerobic growth | + | + | + |
| Acetoin production | + | + | — |
| Glucose (acid | + | + | + |
| L-arabinose (acid) | + | + | + |
| Xyrose | d | + | — |
| Mannitol | d | + | + |
| Casein hydrolysis | d | + | — |
| Gelatin hydrolysis | d | + | — |
| Starch hydrolysis | — | + | (+) |
| Citrate utilization | + | + | — |
| Propionate utilization | d | + | — |
| Tyrosine hydrolysis | — | + | — |
| LV-reaction | — | + | — |
| Indol production | — | + | — |
| Halotolerant | | | |
| 2% | + | + | + |
| 5% | — | + | — |
| 7% | — | + | — |
| 10% | — | ND | — |
| Growth temperature | | | |
| 40° | + | + | + |
| 50° | + | + | + |
| 55° | + | + | + |
| 60° | ND | ND | + |
| 70° | — | — | — |
| Nitrate reduction | d | + | — |
| GC mole % in DNA | 44.5 (Type) 44.3 ~50.3 | 46.4 (Type) 42.9 ~49.9 | 41.9 |

According to the above comparison, the present strain No. 3 has many properties of *Bacillus coagulans* but has specific differences as to acetoin production and GC mole % in DNA. Furthermore, the observation on Litmus milk medium is different (not mentioned in the above comparison).

Accordingly, the present strain has been designated *Bacillus sp. No. 3* and has been deposited on Aug. 16, 1993 at the Fermentation Research Institute, Japan, assigned Deposit No. FERM BP-3013.

According to the present invention, for the production of the enzyme, a myo-inositol dehydrogenase-producing microorganism belonging to genus *Bacillus* is cultured in a suitable medium.

The preferred example of the above myo-inositol dehydrogenase-producing microorganism strain is *Bacillus sp. No. 3*. Since the taxonomical properties of bacteria are in general easily mutated, natural variants or artificial mutants produced by conventional artificial mutation treatment, for example, ultraviolet irradiation, radiation or mutagens such as N-methyl-N-nitro-N-nitrosoguanidine and ethyl methansulfonate, belonging to genus *Bacillus* and having myo-inositol dehydrogenase-producing activity, can be used in the present invention.

Culturing the above microorganisms can be performed under the conventional culture conditions used for bacteria. In the present enzyme production, since myo-inositol dehydrogenase is an enzyme produced from myo-inositol, culture preferably proceeds in a medium containing myo-inositol 0.5–5% to produce myo-inositol dehydrogenase with 10–300 times productivity.

Among the examples of media other than myo-inositol, nutrient media containing assimilable carbon sources, digestible nitrogen sources and if required inorganic salts can be used.

Examples of carbon sources are glucose, fructose or saccharose, used in combination or alone. Examples of digestible nitrogen sources are peptone, meat extract or yeast extract, used in combination or alone. Phosphates, magnesium salts, calcium salts, potassium salts, sodium salts or various heavy metal salts such as ferric salts or manganese salts can also be added. Other known assimilable carbon sources and digestible nitrogen salts can also be used.

Culture can be effected by shake culture or aeration culture with agitation, but for industrial production, submerged aeration culture with agitation is preferable. The culture temperature can be within the usual range for enzyme production and is generally 40–60° C., preferably approximately 50° C.

The culture time depends on the conditions of culture, and can be set for maximum production of the enzyme, and is generally 1–2 days.

The composition of the culture medium, the medium conditions, the culture temperature, agitation speed and air flow should naturally be selected according to known criteria. Anti-foaming agents such as silicone oil and vegetable oil can also be used if desired.

Since the thus-produced myo-inositol dehydrogenase exists as an end enzyme in bacterial cells, cultured cells are collected by means of filtration or centrifugation, and the bacterial cells are decomposed by means of mechanical destruction as by ultrasonication, French press treatment, glass beads treatment or freezing-thawing, or enzymatic digestion such as lysozyme treatment, to obtain a crude extract.

Further purified myo-inositol dehydrogenase can be obtained by known conventional purification methods of isolation of proteins or enzymes. For example, the enzyme can be precipitated by salting out with the addition of ammonium sulfate or sodium sulfate to the crude extract. The precipitated enzyme can further be purified by means of chromatography using molecular sieve and resin, electrophoresis or ultracentrifugation.

The purification can be achieved considering the nature of myo-inositol dehydrogenase. For example, the above precipitate dissolved in water or buffer solution is dialyzed, if required, by semi-permeable membrane, and treated chromatographically using an ion-exchange resin such as DEAE-cellulose, DEAE-Sephacel, DEAE-Sepharose, DEAE-Sephadex, Q-Sepharose (Pharmacia Corp., trade name), DEAE-Toyopearl (Toso Corp.) or hydroxy apatite, hydrophobic chromatographic resin such as octyl-Sepharose or phenyl-Sepharose (Pharmacia Corp.) or other affinity chromatographic resins. Furthermore, molecular sieve chromatography using a gel-filtration agent such as Sephadex G-100 or Sephacryl S-200 can be used. Desalting by means of a semi-permeable membrane can also be performed. A purified myo-inositol dehydrogenase powder can be prepared by lyophilization with the addition of 0.05–10% of stabilizing agent, for example sugars such as mannitol, saccharose or sorbitol, amino acids such as glutamate or glycine, and peptides or such as bovine albumin.

Myo-inositol dehydrogenase of the present invention has the following properties:

1. Substrate specificity:

| | |
|---|---|
| myo-inositol | 100% |
| glucose | 0 |
| fructose | 0 |
| galactose | 0 |
| sorbitol | 0 |
| mannose | 0 |
| maltose | 0 |
| saccharose | 0 |
| lactose | 0 |

2. Enzyme action:

The enzyme catalyzes essentially a reaction of myo-inositol and NAD to generate myo-inosose and reduced NADH, as follows:

myo-inositol+NAD→myo-inosose *+reduced NADH *(2,4,6/3,5-pentahydroxy cyclohexanone)

3. Molecular weight:

130,000±15,000

Measured by TSK-gel G 3000 SW 8 (Toso Corp., 0.75×60 cm).
Elution: 0.1M phosphate buffer (pH 7.0) containing 0.2M NaCl.
Standard: the following molecular markers (Oriental Yeast Co.) are used:

| M.W. | 12,400 | Cytochrome C |
| M.W. | 32,000 | adenylate kinase |
| M.W. | 67,000 | bovine albumin |
| M.W. | 142,000 | lactate dehydrogenase |
| M.W. | 290,000 | glutamate dehydrogenase |

4. Isoelectric point:

pH 4.5±0.5

Measured by electrofocussing using carrier ampholyte at 4° C., 700V, for 40 hours. The activity of a fraction of each enzyme is measured.

5. Km-value: 0.64 mM (myo-inositol), 0.004 mM (NAD)

Km-value for myo-inositol is measured at various concentrations of myo-inositol in a reaction mixture of:

| 100 mM | Tris-HCl buffer (pH 8.5) |
| 5 U | diaphorase (Toyo Jozo Co.0 |
| 1 mM | NAD (Oriental Yeast Co.) |
| 0.025% | NBT (Wake Pure Chem. Co.) |

In the reaction mixture, NAD is replaced by 15 mM myo-inositol, and the concentration of NAD is varied to measure the Km-value for NAD.

The results are as shown above.

Further in the reaction mixture, 1 mM NAD is replaced by 1 mM thio-NAD (Sigma Co. ) and the Km-value for myo-inositol is measured. The result is Km-value: 10.0 mM (myo-inositol).

In the reaction mixture, 1 mM thio-NAD is replaced by 150 mM myo-inositol, and the Km-value for thio-NAD is as follows:

KM-value: 0.17 mM (thio-NAD)

Km-value in the reaction of NADP and myo-inositol are measured. The results are as follows:

Km-value: 0.19 mM (NADP)
Km-value: 30.91 mM (myo-inositol)

Km-values in the reaction of the thio-NADP and myo-inositol are as follows:

Km-value: 2.54 mM (thio-NADP)
Km-value: 179.62 mM (myo-inositol)

As is clearly known hereinabove, the present enzyme can be reacted by using NAD(P) and thio-NAD(P) as the coenzymes.

Figure 4:
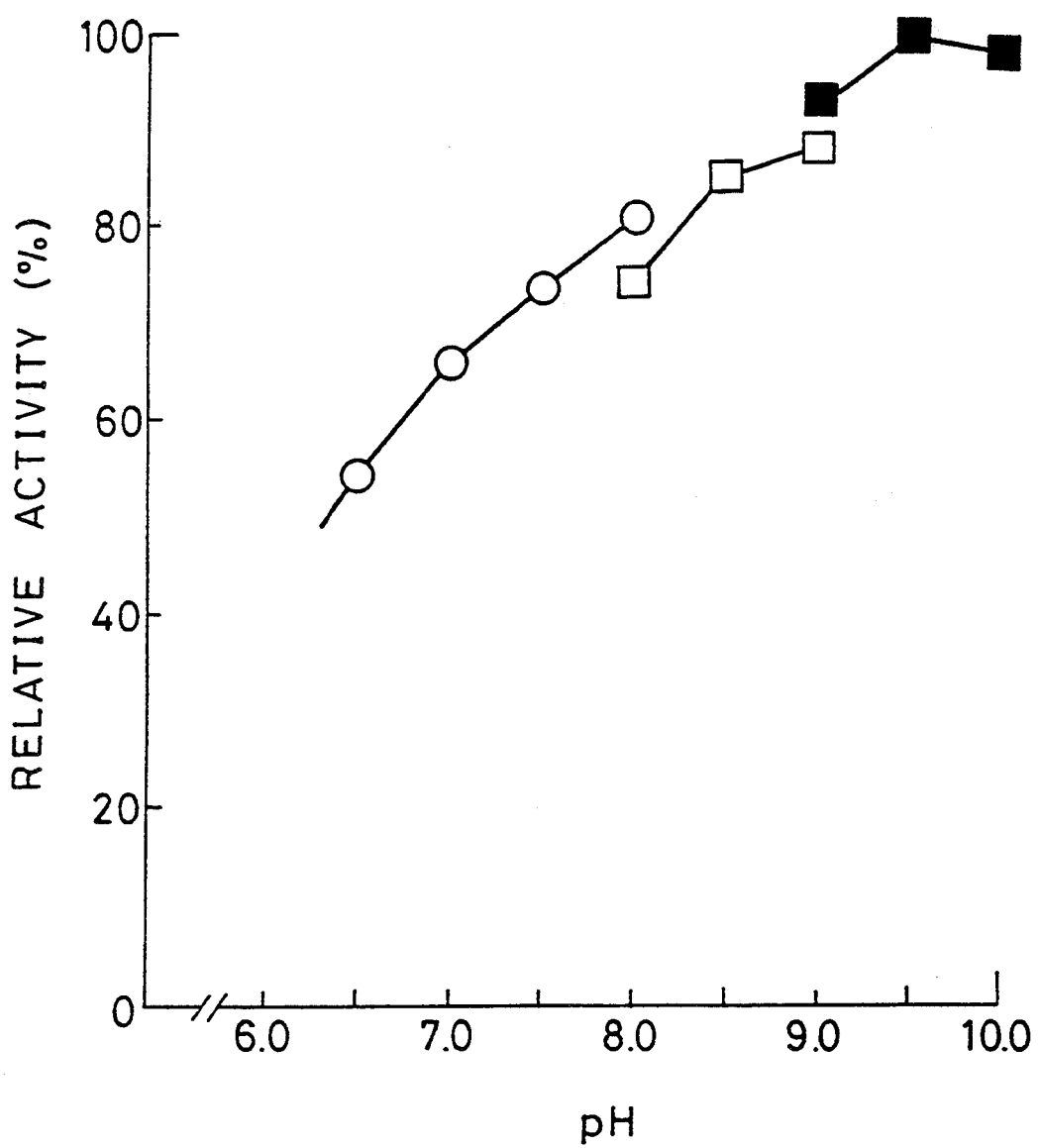
FIG. 4 is a curve of the optimum pH of the myo-inositol dehydrogenase.

6. Optimum pH;

In the assay method for enzyme activity as illustrated hereinafter, 100 mM Tris-HCl buffer (pH 8.5) in the reaction mixture is replaced by 100 mM phosphate buffer (pH 6.5-8.0, —○—), 100 mM Tris-HCl buffer (pH 8.9-9.0, —□— and 100 mM glycine-NaOH buffer (pH 9.0-10.0, —■—), and incubated. The result is shown in FIG. 4.

A maximum activity is observed at approximately pH 9.5.

Figure 3:
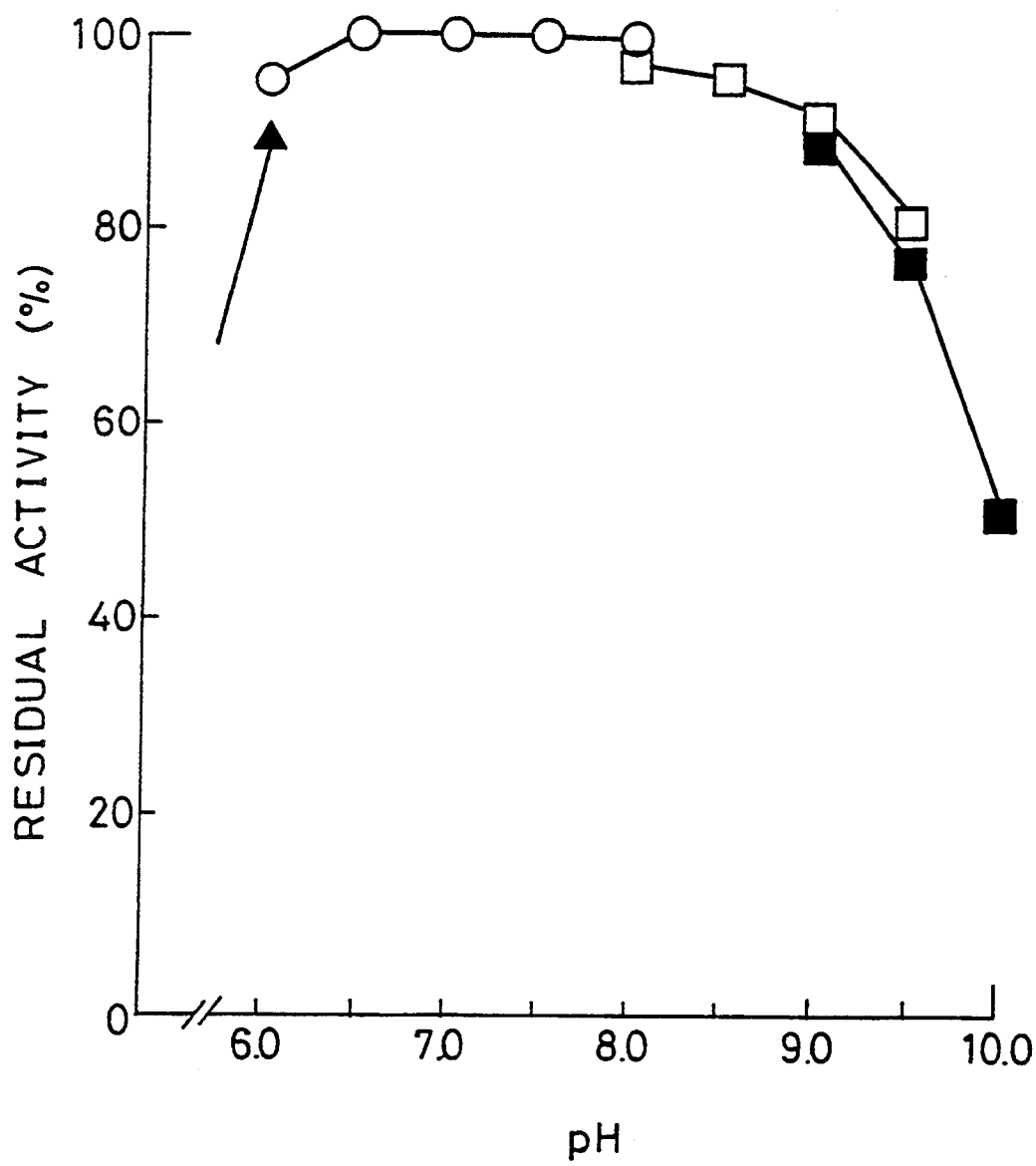
FIG. 3 is a curve of the pH-stability of the myo-inositol dehydrogenase.

7. pH-stability:

The residual activity of the enzyme (1 U/ml, 40 mM buffer solution) is measured in various buffer solutions, i.e., acetate buffer (pH 4.5-6.0, —▲—); phosphate buffer (pH 6.0-8.0, —○—); Tris-HCl buffer (pH 8.0-9.5, —□—)) and glycine-NaOH buffer (pH 9.0-10, —■—) after heating at 50° C. for 15 mins. The enzyme is stable at pH 6.5-9.0 with a residual activity of over 80% as shown in FIG. 3.

8. Heat-stability:

The enzyme, dissolved in 20 mM Tris-HCl buffer (pH 7.0), to produce a 1 U/ml solution, is incubated for 15 mins. at various temperatures, and the residual activity is measured.

The results are as shown in FIG. 1 and the enzyme is stable up to 60° C. with retained residual activity of over 95%.

Figure 2:
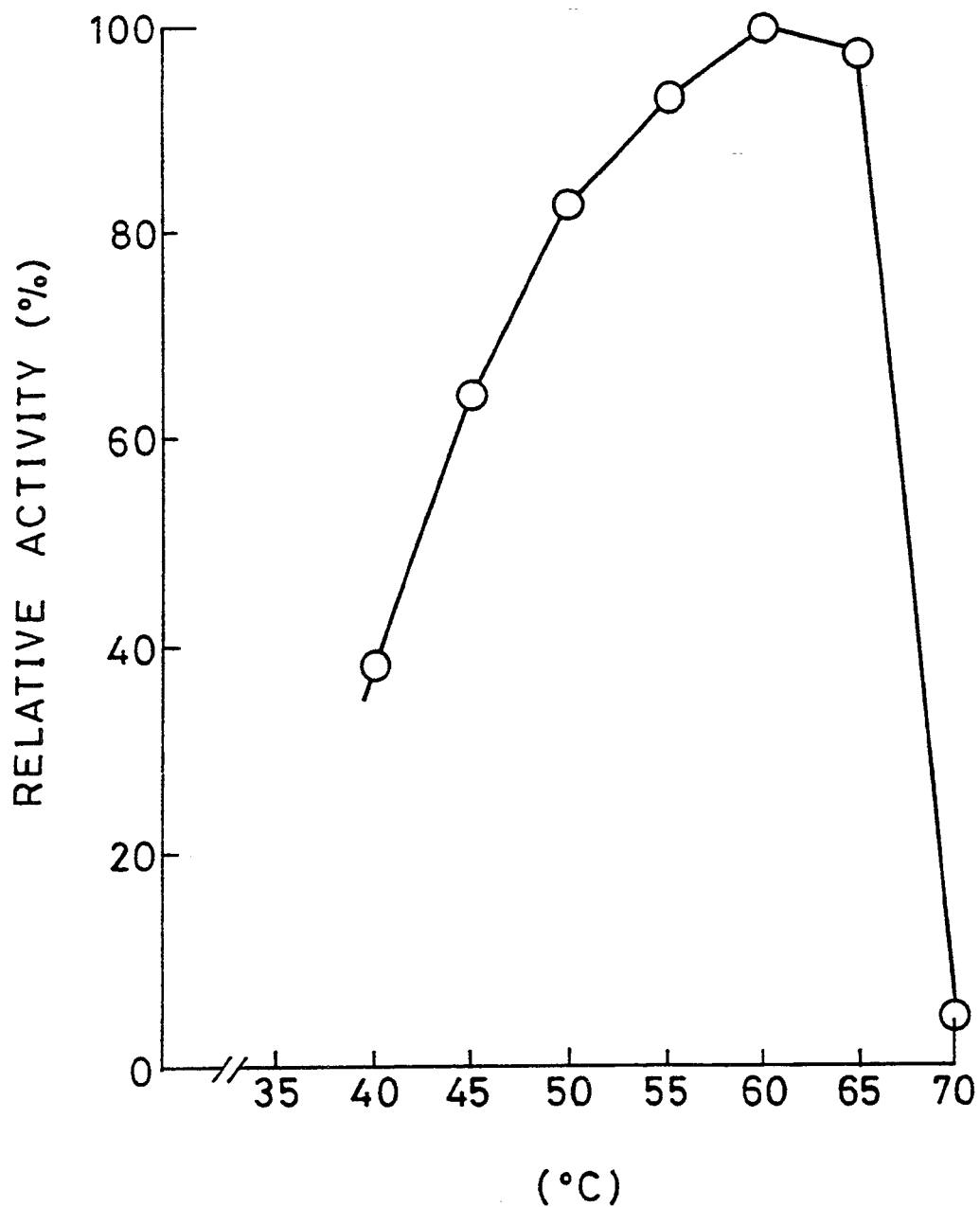
FIG. 2 is a curve of the optimum temperature of the myo-inositol dehydrogenase.

9. Optimum temperature:

The enzyme activity is measured at 35° C., 40° C., 50° C., 55° C., 60° C. and 65° C., respectively, in 100 mM Tris-HCl buffer (pH 8.5) according to the assay method illustrated hereinafter. The reaction was stopped in each case after 10 mins. incubation by adding 0.1N HCl (2 ml), whereupon the optical absorption was measured at 550 nm. The enzyme shows maximum activity at 60° C. as shown in FIG. 2.

10. Assay method of myo-inositol dehydrogenase
(1) Reaction mixture:

| 100 mM | Tris-HCl buffer (pH 8.5) |
| 15 mM | myo-inositol (Wako Pure Chem. Co.) |
| 1 mM | NAD (Oriental Yeast Co.) |
| 5 U | Diaphorase (Toyo Jozo Co.) |
| 0.025% | NBT (Wake Pure Chem. Co.) |

(2) Enzyme Assay:

The above reaction mixture (1 ml) is incubated in a small test tube at 37° C. for 5 mins. Diluted enzyme solution (0.02 ml) is added and the mixture is stirred to initiate the reaction. After exactly 10 mins., 0.1N HCl (2.0 ml) was added and the mixture is stirred to stop the reaction. Absorption at 550 nm ($A_{550}$ nm) is measured to obtain absorption $A_1$. The assay was repeated using the above reaction mixture except that myo-inositol was not included. The mixture is also treated in the same manner as described above and its absorption $A_o$ was measured.

(3) Calculation of enzyme activity:

$$U/ml = \frac{A_1 - A_0}{18.3} \times \frac{1}{10} \times \frac{3.02}{0.02} \times Z$$

wherein
18.3: molecular absorption coefficient (cm²/μmol)
Z: dilution factor

In the enzymatic reaction hereinbefore illustrated, $A_1$ or $B_2$ is the thio-NADP-group, thio-NAD group, NADP group or NAD group of coenzyme. Examples of the thio-NADP group or thio-NAD group are thionicotinamide adenine dinucleotide phosphate (thio-NAD) and thionicotinamide hypoxanthine dinucleotide phosphate or thionicotinamide adenine dinucleotide (thio-NAD) and thionicotinamide hypoxanthine dinucleotide. Examples of the NADP group or NAD group are nicotinamide adenine dinucleotide phosphate (NADP), acetylpyridine adenine dinucleotide phosphate (acetyl NADP) or nicotinamide hypoxanthine dinucleotide phosphate (deamino NADP) and nicotinamide adenine dinucleotide (NAD), acetylpyridine adenine dinucleotide (acetyl NAD) and nicotinamide hypoxanthine dinucleotide (deamino NAD).

In the present invention, when $A_1$ is the thio-NAD(P) group, $B_1$ is the NAD(P)H group, and when $A_1$ is the NAD(P) group, $B_1$ is the thio-NAD(P)H group. Hence at least one will be a thio-type coenzyme.

Furthermore, when the thio-NAD group and the NAD group are coenzymes of myo-inositol dehydrogenase, any of thio-NAD group and NAD group hereinabove illustrated can be selected. Furthermore, when thio-NAD(P) group and NAD(P) group are coenzymes of the enzyme, any of thio-NAD group or thioNADP group and NAD group or NADP group can be selected.

In a composition for the assay of myo-inositol according to the present invention, the concentration of $A_1$ and $B_1$ is 0.02–100 mM, preferably 0.05–20 mM, and the concentration of myo-inositol dehydrogenase is 5–1000 U/ml, preferably 2–500 U/ml. Amounts exceeding the above ranges are acceptable though wasteful.

$A_1$ and $B_1$ are used in excess as compared with myo-inositol and are in excess as compared with the Km-value (mM) of myo-inositol dehydrogenase for $A_1$ and $B_1$. Specifically a 20–10,000 times molar excess relative to myo-inositol is preferred.

In the present invention, the fourth component of a second dehydrogenase which does not act on myo-inositol and which constitutes a reaction from $B_2$ to $B_1$, and a substrate for the said second dehydrogenase, are combined to effect a cycling reaction (II) in which a reaction for regenerating the $B_1$ is added to the reaction $B_1 \rightarrow B_2$, and the amount of $A_2$ generated is measured.

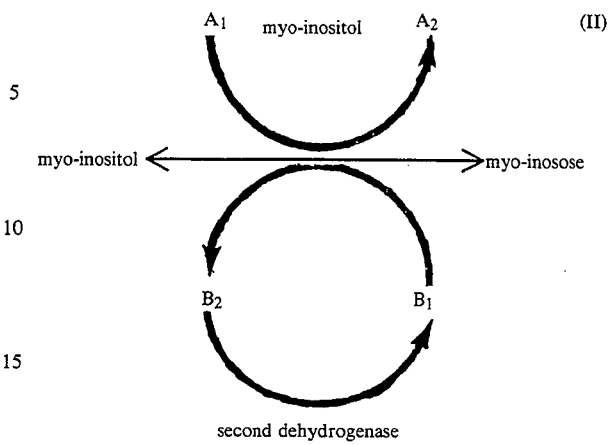

second dehydrogenase wherein $A_1$ is a thio-NADP group, thio-NAD group NADP group or NAD group, $A_2$ is a reduced form of $A_1$, when $A_1$ is a thio-NADP group or thio-NAD group, $B_1$ is a reduced NADP group or reduced NAD group and when $A_1$ is an NADP group or NAD group, $B_1$ is a reduced thio-NADP group or reduced thio-NAD group, and wherein $B_2$ is an oxidized form of $B_1$, and the reaction from $B_2$ to $B_1$ is an enzymatic reaction which regenerates $B_1$ by the action of the second dehydrogenase with the coenzyme of $B_2$. Namely, the second dehydrogenase is added supplementarily for regenerating the $B_1$, and thus the amount of $B_1$ can be reduced. $B_1$ can be replaced by $B_2$ or a mixture of $B_1$ and $B_2$. In this case the amount of $B_1$ or/and $B_2$ is not limited, but is generally below 1/10 mole as to $A_1$, preferably 1/50–1/1000 mole, or less.

In a composition for the assay of myo-inositol using component (4) according to the present invention, the concentration of $A_1$ is 0.02–100 mM, preferably 0.05–20 mM, the concentration of $B_2$ or/and $B_1$ is 0.05–5000 μM, preferably 5–500 μM, and the concentration of myo-inositol dehydrogenase is 5–1000 U/ml, preferably 20–500 U/ml. The concentration of the second dehydrogenase is 20 times (U/ml) or more as compared with the Km-value of the second myo-inositol dehydrogenase for $B_2$, for example preferably 1–100 U/ml. The substrate for the second dehydrogenase is used in excess, preferably 0.05–20 mM or more.

Examples of the second dehydrogenase and a substrate for the second dehydrogenase are as follows:

$B_2$: NAD group or thio-NAD group;
Alcohol dehydrogenase (EC.1.1.1.1) and ethanol,
Glycerol dehydrogenase (EC.1.1.1.6) (E. coli) and glycerol,
Glycerol-3-phosphate dehydrogenase (EC.1.1.1.8) (rabbit muscle) and L-glycerol-3-phosphate,
Maleic dehydrogenase (EC.1.1.1.37) (porcine heart muscle, bovine heart muscle) and L-malate, and
Glyceraldehyde phosphate dehydrogenase (EC.1.2.1.12) (rabbit muscle, liver, yeast, E. coli) and D-glyceraldehyde phosphate and phosphate.

$B_2$: NADP group or thio-NADP group;
Glucose-6-phosphate dehydrogenase (EC.1.1.1.49) (yeast) and glucose-6-phosphate,
Isocitrate dehydrogenase (EC.1.1.1.42) (yeast, porcine heart muscle) and isocitrate,
Glyoxylate dehydrogenase (EC.1.2.1.17) (Pseudomonas oxalaticus) and CoA and glyoxylate,
Phosphogluconate dehydrogenase (EC.1.1.1.44) (rat liver, beer yeast, E. coli) and 6-phosphogluconate, Glyceraldehyde dehydrogenase (EC.1.2.1.13) (chlorophyll) and D-glyceraldehyde-3-phosphate and phosphate and Benzaldehyde dehydrogenase (EC.1.2.1.7) (Pseudomonas fluorescens) and benzaldehyde.

In the present invention, a 5th component of a third dehydrogenase which does not act on myo-inositol and which promotes a reaction from $A_2$ to $A_1$, and a substrate for the said third dehydrogenase are combined to effect a cycling reaction (III) in which a reaction for regenerating the $A_1$ is added to the reaction $A_1A_2$, and the decrease of $B_1$ is measured.

a third dehydrogenase

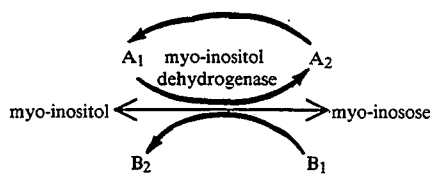

wherein $A_1$ is a thio-NADP group, thio-NAD group, NADP group or NAD group, $A_2$ is a reduced form of $A_1$, when $A_1$ is a thio-NADP group or thio-NAD group, $B_1$ is a reduced NADP group or reduced NAD group and when $A_1$ is an NADP group or NAD group, $B_1$ is a reduced thio-NADP group or reduced thio-NAD group, and wherein $B_2$ is an oxidized form of $B_1$, and the reaction from $A_2$ to $A_1$ is an enzymatic reaction which regenerates $A_1$ by the action of the third dehydrogenase with coenzymes of $A_2$. Namely, the third dehydrogenase is added supplementarily for regenerating the $A_1$, and the amount of $A_1$ can be reduced. $A_1$ can be replaced by $A_2$ or a mixture of $A_1$ and $A_2$. In this case the amount of $A_1$ or/and $A_2$ is not limited, but is generally below 1/10 mole as is $B_1$, preferably 1/50–1/1000 mole, or less.

In a composition for the assay of myo-inositol using the component (5) according to the present invention, the concentration of $B_1$ is 0.02–100 mM, preferably 0.05–20 mM, the concentration of $A_2$ or/and $A_1$ is 0.05–5000 μM, preferably 5–500 μM, and the concentration of myo-inositol dehydrogenase is 5–1000 U/ml, preferably 20–500 U/ml. The concentration of the third dehydrogenase is 20 times (U/ml) or more as compared with the Km-value of the third myo-inositol dehydrogenase for $A_2$, for example preferably 1–100 U/ml. The substrate for the third dehydrogenase is used in excess, preferably 0.05–20 mM or more.

Examples of the third dehydrogenase and a substrate for the third dehydrogenase are as follows:

$A_1$: NAD group or thio-NAD group;

Alcohol dehydrogenase (EC.1.1.1.1) and acetoaldehyde,

Glycerol dehydrogenase (EC.1.1.1.6) (E. coli) and dihydroxyacetone,

Glycerol-3-phosphate dehydrogenase (EC.1.1.1.8) (rabbit muscle) and dihydroxyacetone phosphate, Maleic dehydrogenase (EC.1.1.1.37) (porcine heart muscle, bovine heart muscle) and oxaloacetate and Glyceraldehyde phosphate dehydrogenase (EC.1.2.1.12) (rabbit muscle, liver, yeast, E. coli) and 1,3-diphospho-D-glycerate.

$A_1$: NADP group or thio-NADP group;

Glucose-6-phosphate dehydrogenase (EC.1.1.1.49) (yeast) and gluconolactone-6-phosphate, and Glyceraldehyde phosphate dehydrogenase (EC.1.2.1.13) (chlorophyll) and 1,3-diphospho-D-glycerate.

The myo-inositol dehydrogenase used in the composition for assay of myo-inositol according to the present invention can be an enzyme having reactivity on a substrate of myo-inositol together with a suitable coenzyme NAD group, preferably an NAD or thio-NAD group, preferably a thio-NAD and NADP group, preferably an NADP or thio-NADP group, preferably thio-NADP. Its suitability can be confirmed by using the said coenzyme and substrate.

In the composition of the reaction medium, two coenzymes are selected by considering the relative activity of myo-inositol dehydrogenase on each coenzyme. Thereafter, the pH condition thereof at each optimum pH of the forward reaction and reverse reaction is adjusted to fix the pH-condition wherein a ratio of reaction rate of the forward reaction and reverse reaction approaches 1.

Myo-inositol dehydrogenase produced by Bacillus sp. No. 3 (product of Toyo Jozo Co.) has a relative activity of approximately 10–15% when coenzyme thio-NAD is used, as compared to the use of NAD. The optimum pH is approximately 9.5 for the forward reaction and approximately 7–7.5 for the reverse reaction. The enzyme can utilize both the NAD group and the NADP group as coenzyme.

In the present invention, myo-inositol dehydrogenase from a single origin or from plural origins can be used.

Myo-inositol in a specimen can be assayed by adding 0.001–0.5 ml of a specimen to the assay composition containing the above components (1)–(3), components (1)–(4) or components (1)–(3) and (5), reacting at approximately 37° C., then measuring the amount of generated $A_2$ or consumed $B_1$ over an interval spanning two time points after starting the reaction, for example one minute between 3 mins. and 4 mins. after starting, or five minutes between 3 mins and 8 mins. after starting the reaction. Measurement is effected by determining the changes of absorption at each of a plurality of optical wavelengths. For example, when $A_2$ is thio-NADH and $B_1$ is NADH, generated $A_2$ is measured by an increase of absorption at 400 nm or consumed $B_1$ is measured by a decrease of absorption at 340 nm and the thus-obtained value is compared with the value of a known or reference concentration of myo-inositol, whereby the concentration of myo-inositol in a specimen can be measured in real time.

According to the assay method of the present invention, since myo-inositol already existing in a specimen is introduced into the enzymatic cycling reaction, it is little affected by any coexisting substances in the specimens, and hence a measurement of a blank value of the specimen is not required. Thus, a simple assay system using a rate assay can be achieved.

In the present invention, measuring the value of $A_2$ or $B_1$ can be performed not only by absorbency, but also by other known analytical methods instead.

As explained above, the present invention has advantages in that no measurement error can occur, due to the use of coenzymes each having a different absorption in its reduced form, and in that the amounts of myo-inositol can also be assayed precisely and rapidly with even a small amount of specimen, due to the combining enzymatic cycling reaction. In the present invention, the use of heat stable myo-inositol dehydrogenase having a residual activity over 95% at 65° C. is preferred.

EXAMPLES

The following examples illustrate the present invention but are not to be construed as limiting.

EXAMPLE 1

Reagents:

| | |
|---|---|
| 40 mM | Glycine-NaOH buffer (pH 10.0) |
| 2 mM | Thio-NAD (Sankyo Co.) |
| 0.2 mM | reduced NAD (Oriental Yeast Co.) |
| 150 U/ml | Myo-inositol dehydrogenase (Toyo Jozo Co. Bacillus sp. No. 3) |

Figure 5:
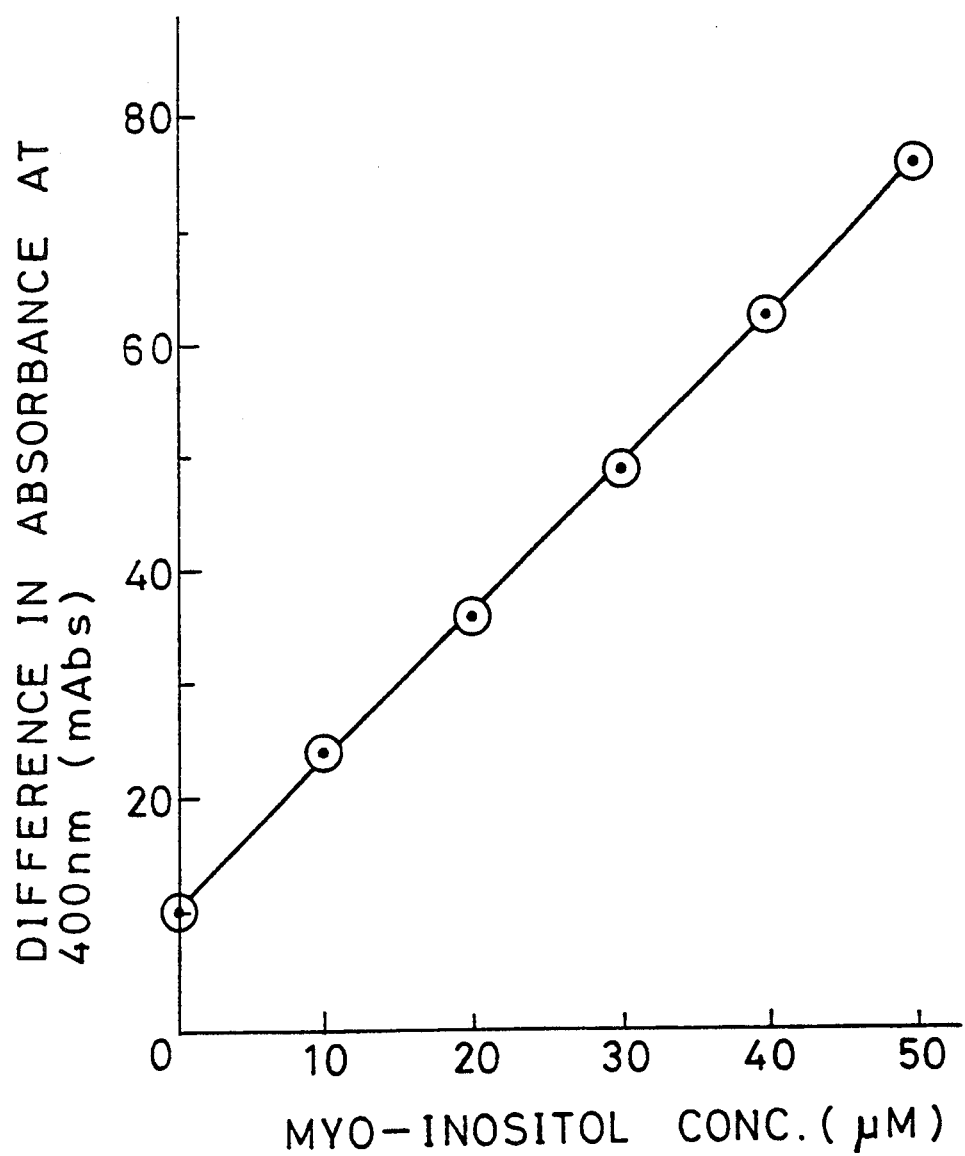
FIGS. 5-8 are assay curves of myo-inositol.

Procedure:

The above reagent mixture (1 ml) was put into cuvettes and 20 μl of each of a range of concentrations of myo-inositol solution (0, 10, 20, 30, 40 and 50 μM, respectively) was added thereto, with the reaction temperature at 37° C. After incubation commenced the difference in absorbance at 400 nm at 2 mins. and 7 mins. was measured. The results are shown in FIG. 5, from which it can be seen that a linear relation between the amount of myo-inositol and the change in absorption was observed.

EXAMPLE 2

Reagents:

| | |
|---|---|
| 40 mM | Glycine-NaOH buffer (pH 9.5) |
| 2 mM | Thio-NAD (Sankyo Co.) |
| 0.1 mM | reduced deamino NAD (Sigma Co.) |
| 200 U/ml | Myo-inositol dehydrogenase (Toyo Jozo Co. Bacillus sp. No. 3) |

Figure 6:
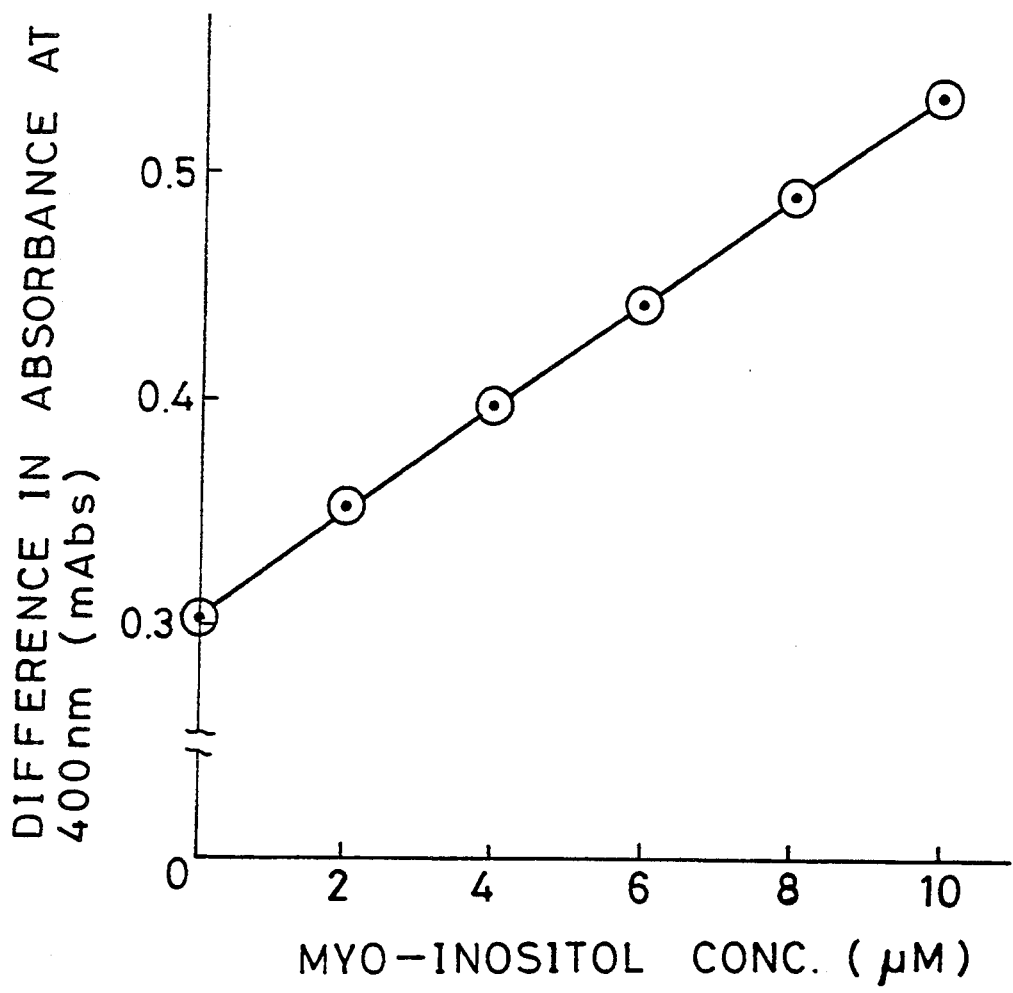

Procedure:

The above reagent mixture (1 ml) was put into cuvettes and 50 μl of each of a range of concentrations of myo-inositol solution (0, 2, 4, 6, 8 and 10 μM, respectively) was added thereto, then the mixture was incubated at 37° C. for 60 minutes. Then the reaction was stopped by adding 0.5% sodium dodecyl sulfate (1 ml). Absorbance at 400 nm was measured. The results are shown in FIG. 6, from which it can be seen that a good linear quantitative curve was obtained.

EXAMPLE 3

Reagents:

| | |
|---|---|
| 50 mM | Glycine-NaOH buffer (pH 10.0) |
| 0.2 mM | reduced NAD (Oriental Yeast Co.) |
| 4 mM | thio-NAD (Sankyo Co.) |
| 250 U/ml | Myo-inositol dehydrogenase (Toyo Jozo Co. Bacillus sp. No. 3) |
| 0.2% | Triton X-200 |

Procedure:

The above reagent mixture (1 ml) was put into cuvettes and 20μl of each of three different sera was added thereto, with the reaction temperature at 37° C. After incubation commenced, the difference in absorbance at 400 nm at 5 mins. and 6 mins. was measured.

50 μM myo-inositol solution (standard solution) and distilled water (reagent blank) were treated in the same manner as above and the amount of myo-inositol in serum samples was calculated from the difference in absorbance between the standard solution and samples.

In the Table hereinbelow, the results obtained from three different sera are shown.

| | Difference in Absorbance (mAbs) | Myo-inositol Concentration |
|---|---|---|
| Reagent blank | 2 | — |
| Standard solution | 29 | 50 μM |
| Serum 1 | 25 | 42.6 μM |
| Serum 2 | 21 | 35.2 μM |
| Serum 3 | 31 | 53.7 μM |

EXAMPLE 4

Reagents:

| | |
|---|---|
| 40 mM | Glycine-NaOH buffer (pH 10.0) |
| 15 mM | NADP (Oriental Yeast Co.) |
| 50 μM | Thio-NAD (Sankyo Co.) |
| 0.4 M | Ethanol |
| 30 U/ml | Alcohol dehydrogenase (Oriental Yeast Co.) |
| 250 U/ml | Myo-inositol dehydrogenase (Toyo Jozo Co. Bacillus sp. No. 3) |

Figure 7:
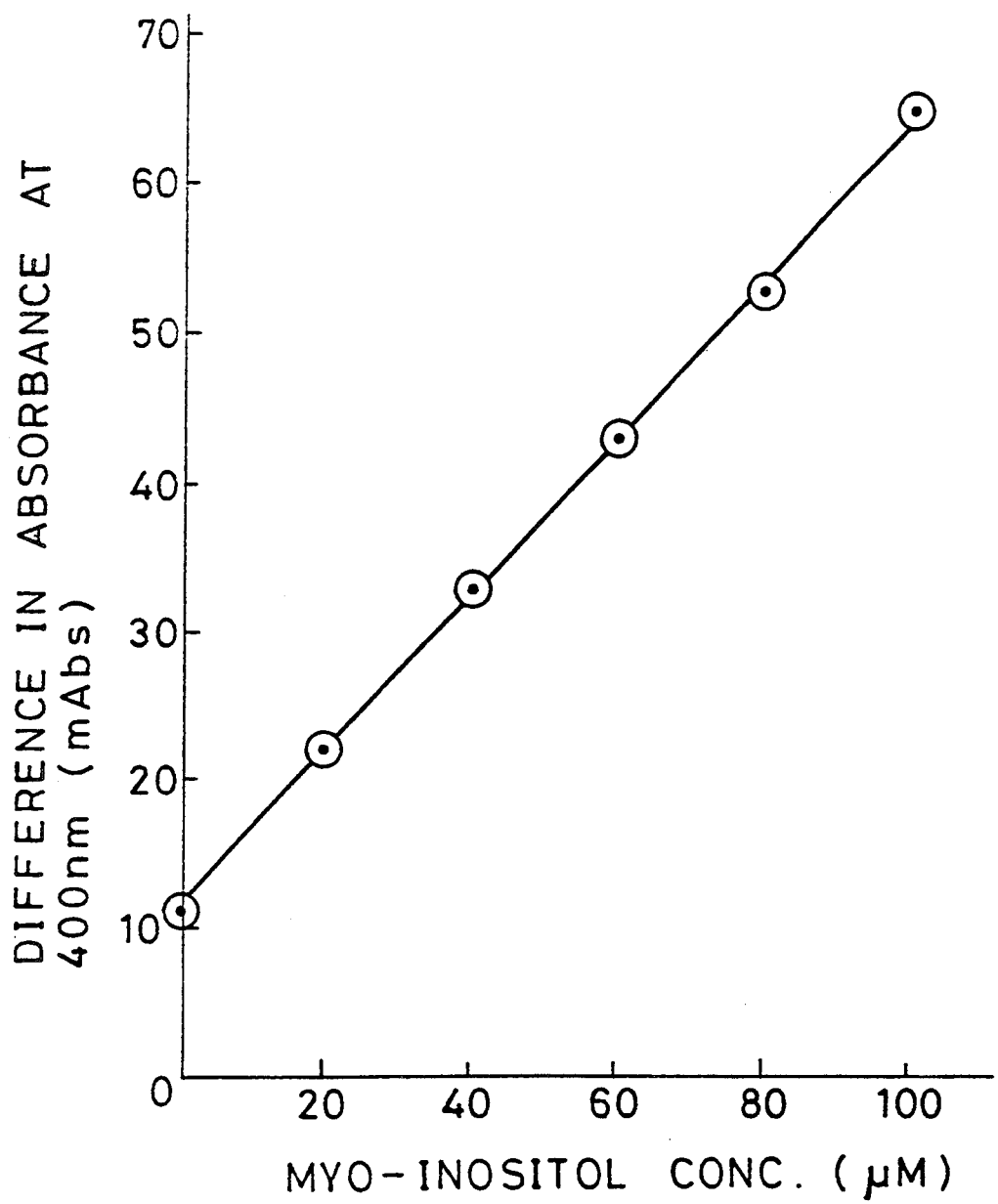

Procedure:

The above reagent mixture (1 ml) was put into cuvettes and 50 μl of each of concentrations of myo-inositol solution (0, 20, 40, 60, 80 and 100 μM, respectively) was added thereto, with the reaction temperature at 37° C. After incubation commenced, the difference in absorbency at 340 nm at 3 mins. and 8 mins. was measured. The results are shown in FIG. 7.

EXAMPLE 5

Reagents:

| | |
|---|---|
| 50 mM | Phosphate buffer (pH 7.0) |
| 0.25 mM | reduced NADP (Oriental Yeast Co.) |
| 50 μM | thio-NAD (Sankyo Co.) |
| 5 mM | Dihydroxyacetone phosphate |
| 10 U/ml | Glycerol-3-phosphate dehydrogenase (Boehringer Mannheim, rabbit muscle) |
| 250 U/ml | Myo-inositol dehydrogenase (Toyo Jozo Co. Bacillus sp. No. 3) |

Figure 8:
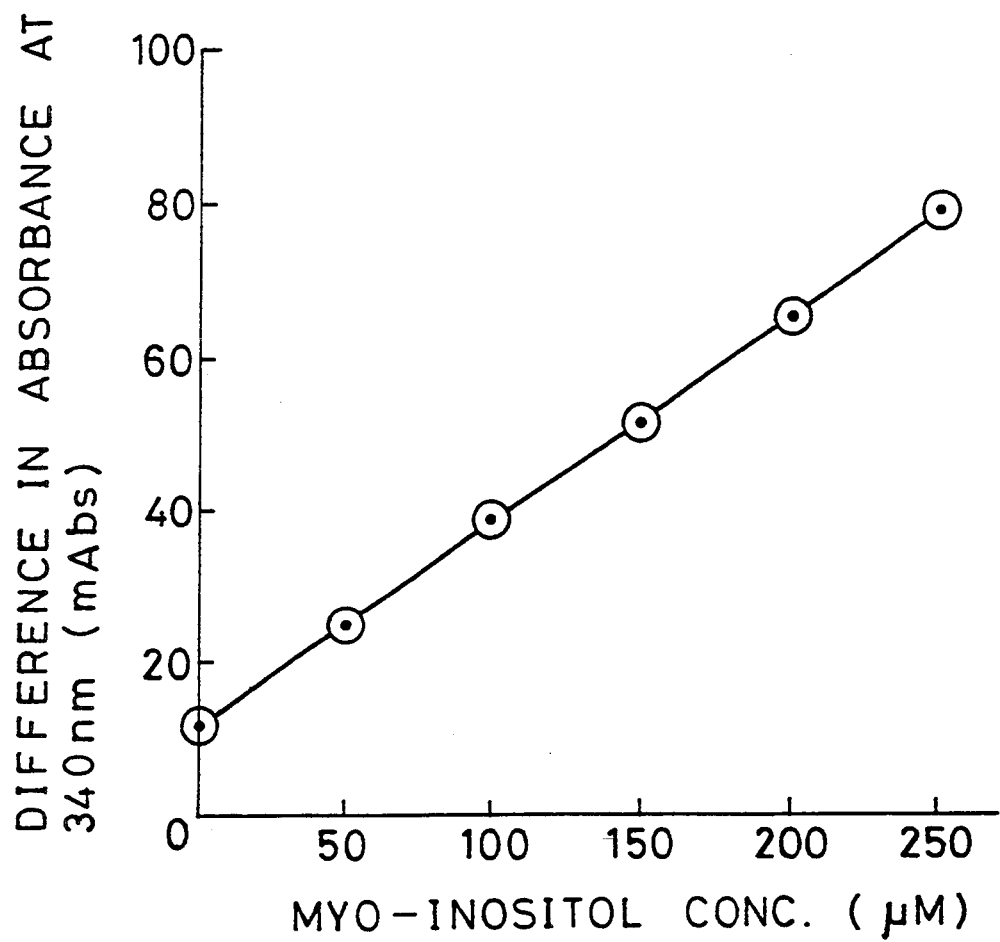

Procedure:

The above reagent mixture (1 ml) was put into cuvettes and 50 μl of each of concentrations of myo-inositol solution (0, 50, 100, 150, 200 and 250 μM, respectively) was added thereto, with the reaction temperature at 37° C. After incubation commenced, the difference in absorbance at 340 nm at 3 mins. and 8 mins. was measured. The results are shown in FIG. 8.

EXAMPLE 6

Culture Bacillus sp. No. 3:

| | |
|---|---|
| Yeast extract (Kyokuto Seiyaku Co.) | 2% |
| Peptone (Kyokuto Seiyaku Co.) | 2% |
| K$_2$HPO$_4$ (Wako Pure Chem. Co.) | 0.2% |
| CaCl$_2$ (Wako Pure Chem. Co.) | 0.02% |
| MgSO$_4$.7H$_2$O (Wako Pure Chem. Co.) | 0.05% |
| Myo-inositol (Wako Pure Chem. Co.) | 2% |
| pH 7.3 | |

100 ml of a liquid medium comprising the above composition was sterilized in a 500 ml Erlenmeyer flask at 120° C. for 20 mins. One loopful of Bacillus sp. No. 3 was inoculated into the medium and the medium was cultured at 50° C. with stirring at 120 r.p.m. for 30 hours to obtain the cultured mass (85 ml) (enzyme activity: 1.2 U/ml). 20 l of a liquid medium comprising the above composition to which was added disform CB 442 (Nihon Yushi Co.) 0.1% was sterilized in a 30 l jar fermenter by heating. 85 ml of the pre-cultured seed culture obtained in the step above was inoculated therein and the mixture was cultured at 50° C., with aeration of 20 l/ml, inner pressure 0.4 kg/cm², and agitation at 150 r.p.m. for 24 hours to obtain the cultured mass (18.0 l ) (enzyme activity: 1.8 U/ml).

EXAMPLE 7

Purification of enzyme

Bacterial cells collected by centrifugation from the cultured broth obtained in Example 6 were suspended in 20 mM phosphate buffer (pH 7.5, 5 l) containing 0.1% lysozyme (Eizai Co.) and solubilized at 37° C. for 1 hour; then the mixture was centrifuged to remove precipitate and to obtain a supernatant solution (4500 ml) (activity: 6 U/ml). Acetone (1.8 l) was added to the supernatant solution to separate the precipitate, which was dissolve din 20 mM phosphate buffer to obtain a crude extract (1 lit., 24.2 U/ml).

Ammonium sulfate (200 g) was added to the solution, which was mixed well by stirring and then centrifuged to separate the precipitate. An additional 250 g ammonium sulfate was then added to the supernatant solution, and the solution was centrifuged to obtain a new precipitate. The new precipitate was dissolve din 20 mM phosphate buffer (pH 7.5) to obtain an enzyme solution (500 ml, specific activity 36.3 U/ml), and the resultant solution was dialyzed overnight against 20 mM phosphate buffer (pH 7.5, 20 lit.) The dialyzed enzyme solution was charged on a column of DEAE-Sepharose CL-6B (Pharmacia Co.) (250 ml) which was bufferized with 20 mM phosphate buffer (pH 7.5), washed with 20 mM phosphate buffer containing 0.1M KCl, (pH 7.5, 1 lit) and eluted with 20 mM phosphate buffer containing 0.3M KCl (pH 7.5) to obtain an enzyme solution (350 ml, activity 35.2 U/ml ). The enzyme solution was dialyzed overnight against 10 mM phosphate buffer (pH 7.0, 20 lit.) Bovine serum albumin (Sigma Co., 02. g) was dissolved in the thus-obtained enzyme solution, then the solution was lyophilized to obtain the lyophilized enzyme (1.1 g, 10.6 U/mg).

What is claimed is:

1. A method of assaying myo-inositol comprising reacting a specimen containing myo-inositol with the following reagents:
   a) myo-inositol dehydrogenase which, in the presence of a thionicotinamide adenine dinucleotide group (thio-NAD-group) and a nicotinamide adenine dinucleotide group (NAD group) as coenzymes, catalyzes a reversible reaction forming myo-inosose from myo-inositol,
   b) $A_1$ and
   c) $B_1$; to effect a cycling reaction

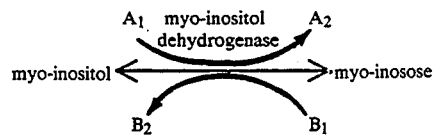

wherein $A_1$ is a thio-NAD group or NAD group, $A_2$ is a reduced form of $A_1$, when $A_1$ is a thio-NAD group, $B_1$ is a reduced NAD group and when $A_1$ is an NAD group, $B_1$ is a reduced thio-NAD group, and wherein $B_2$ is an oxidized form of $B_1$; and measuring a change in the amount of $A_2$ generated or $B_1$ consumed by the cycling reaction wherein $A_1$ and $B_1$ are each used at a concentration of 0.02–100 mM, and wherein said myo-inositol dehydrogenase is used at a concentration of 5–1000 U/ml.

2. The assay method according to claim 1, wherein said thio-NAD group is thionicotinamide adenine dinucleotide (thio-NAD) or thionicotinamide hypoxanthine dinucleotide.

3. A reagent composition for assaying myo-inositol, comprising:
   a) myo-inositol dehydrogenase which, in the presence of a thionicotinamide adenine dinucleotide group (thio-NAD group) and a nicotinamide adenine dinucleotide group (NAD group) as coenzymes, catalyzes a reversible reaction forming myo-inosose from myo-inositol,
   b) $A_1$ and
   c) $B_1$; wherein $A_1$ is a thio-NAD group or NAD group, when $A_1$ is a thio-NAD group, $B_1$ is a reduced form of an NAD group, and when $A_1$ is an NAD group, $B_1$ is a reduced form of a thio-NAD group
   wherein $A_1$ and $B_1$ are each present in a concentration of 0.02–100 mM, and wherein said myo-inositol dehydrogenase is present in a concentration of 5–1000 U/ml.

4. Myo-inositol dehydrogenase having the following properties:
   substrate spcificity for myo-inositol and
   catalyzes a reaction
   myo-inositol + NAD ~ myo-inosose + reduced NADH, said myo-inositol dehydrogenase having the following physicochemical properties:
   (1) molecular weight: 130,000 ± 15,000 (gel filtration method by TSK gel G 3000 SW)
   (2) iso-electric point: pH 4.5 ± 0.5
   (3) Km-value:
      Km value for myo-inositol: 0.64 mM
      Km value for NAD: 0.004 mM
   (4) optimum pH: approximately ph. 9.5
   (5) pH-stability: more than 80% retained activity at pH 6.5–9.0.

5. A process for the production of myo-inositol dehydrogenase which comprises culturing a myo-inositol dehydrogenase-producing microorganism belonging to genus Bacillus, and isolating myo-inositol hydrogenase from the cultured mass, wherein the myo-inositol dehydrogenase-producing microorganism belonging to genus Bacillus is Bacillus sp. No. 3(FERM BP-3013).

* * * * *